United States Patent
Wang

[19]

[11] Patent Number: 6,106,497
[45] Date of Patent: Aug. 22, 2000

[54] SYSTEM AND METHOD FOR PREVENTING AN AIR EMBOLISM IN A SURGICAL PROCEDURE

[75] Inventor: Carl C. T. Wang, Oakland, Calif.

[73] Assignee: Medical Instrument Development Laboratories, San Leandro, Calif.

[21] Appl. No.: 09/015,168

[22] Filed: Jan. 29, 1998

Related U.S. Application Data

[60] Provisional application No. 60/037,265, Jan. 31, 1997.

[51] Int. Cl.[7] .................................................. A61M 1/00
[52] U.S. Cl. ............................................. 604/122; 604/26
[58] Field of Search ................................ 604/26, 23, 122

[56] References Cited

U.S. PATENT DOCUMENTS

| | | | |
|---|---|---|---|
| 3,858,572 | 1/1975 | Binard et al. | |
| 4,280,495 | 7/1981 | Lampert | 128/214 |
| 4,319,580 | 3/1982 | Colley et al. | 128/661 |
| 4,354,500 | 10/1982 | Colley et al. | 128/663 |
| 4,354,502 | 10/1982 | Colley et al. | 128/663 |
| 4,985,014 | 1/1991 | Orejola | 600/16 |
| 5,011,469 | 4/1991 | Buckberg et al. | 604/4 |
| 5,139,478 | 8/1992 | Koninckx et al. | 604/26 |
| 5,169,378 | 12/1992 | Figuera | 600/16 |
| 5,249,579 | 10/1993 | Hobbs et al. | 128/662.02 |
| 5,401,255 | 3/1995 | Sutherland et al. | 604/247 |
| 5,411,474 | 5/1995 | Ott et al. | 604/26 |
| 5,573,502 | 11/1996 | LeCocq et al. | 604/4 |
| 5,670,177 | 9/1997 | Briend et al. | 424/718 |
| 5,849,005 | 12/1998 | Garrison et al. | 604/26 X |

FOREIGN PATENT DOCUMENTS

| | | | |
|---|---|---|---|
| 2323682 | 11/1974 | Germany | 604/26 |
| 3000218 | 7/1981 | Germany | 604/26 |
| 1727794 | 4/1992 | U.S.S.R. | 604/26 |
| 94/13204 | 6/1994 | WIPO | 604/26 |

*Primary Examiner*—Jeffrey A. Smith
*Attorney, Agent, or Firm*—Nicholas A. Kees; Godfrey & Kahn, S.C.

[57] ABSTRACT

A system and method is provided for preventing the development of an air embolism in an animal during and after a cardiovascular surgical procedure. Also provided is a device that can accurately control the pressure and/or flow of gas into the heart cavity and related blood vessels.

34 Claims, 6 Drawing Sheets

Surgical procedure using the present system

Open pericardium & suture to chest cannulate aorta & connect to arterial return of heart/lung machine cannulate right heart & connect to venous outflow begin bypass place cardioplegia line into aorta

A) FOR AORTIC VALVE REPLACEMENT place sump/CO2 conveying line into left ventricle

- through left atrium then crossing mitral valve, or
- through the apex of the heart, or
- in the left atrium, or
- sump line placed in the pulmonary artery & separate CO2 line in the left ventricle

B) FOR MITRAL VALVE REPLACEMENT place sump/CO2 conveying line into left atrium, or through mitral valve into left ventricle CONSOLE PRESSURE SET @ "NORMAL, LOW FLOW" mode -- CO2 line primed prior to placement clamp aorta place cardioplegia into the root decompress heart via sump cool heart CONSOLE PRESSURE SET "NORMAL, HIGH FLOW" MODE DURING
THIS PHASE OF SURGERY WHILE VALVE EXPOSED expose valve remove valve insert valve — if significant air trapped in heart ⟶ partially close surgical wound
                                                                                                CO2 PRESSURE SET @ "AIR PURGE" mode
                                                                                                activate sump line to remove bload/foam from L.V.
                                                                                                let gas escape through cardioplegia incision fill heart with blood & remove air (gas)
                                                           partially close surgical wound
                                                           RESET CO2 PRESSURE@ "NORMAL, HIGH FLOW"
                                                           MODE close surgical wound ⟵ fill heart with blood as gas escapes through incision

CONSOLE PRESSURE SET @ "NORMAL, LOW FLOW" MODE remove aortic clamp & resuscitate heart remove sump line from the left ventricle close venting hole in the aorta stop heart lung machine

FIG. 8

Alternate surgical procedure using the present system.

open pericardium & suture to chest cannulate aorta & connect to heart/lung machine cannulate right heart & connect to venous outflow begin bypass place cardioplegia line into aorta clamp aorta place cardioplegia into the root cool heart expose valve remove valve insert valve ———— if significant air trapped in heart ————▶ Place double lumen CO2/air exchange tubing from surgical wound:

PLACE SUMP/CO2 LINE INTO LEFT VENTRICLE a) through aorta for aortic valve replacement, or
    b) through left atrium and left ventricle for mitral valve replacement partially close surgical wound CO2 PRESSURE SET @ "AIR PURGE" mode activate sump line to remove blood & foam from left heart    infuse CO2 @ "AIR PURGE" mode setting to displace let gas mix escape through cardioplegia incision ( 2 mins.)    trapped air while closing the wound partially close surgical wound RESET CO2 CONSOLE @ "NORMAL, HIGH FLOW" mode fill heart with blood as gas escapes through incision close surgical wound SET CO2 PRESSURE @ 15mmHg after the wound is closed ◂————┘ remove aortic clamp & resuscitate heart remove sump line from the left ventricle close venting hole in the aorta stop heart lung machine remove vena cava tube remove aortic cannula

FIG. 9

SYSTEM AND METHOD FOR PREVENTING AN AIR EMBOLISM IN A SURGICAL PROCEDURE

This application claims benefit to U.S. provisional application Ser. no. 60/037,265 filed Jan. 31, 1997.

BACKGROUND OF THE INVENTION

Systemic air embolisms have long been recognized as a complication of cardiovascular surgery. There are various procedures that are presently used to dislodge trapped air from the heart in an attempt to prevent or minimize this occurrence including manually manipulating the heart, and tipping or rotating the body of the patient. However, current procedures are time-consuming and often incomplete in removing trapped air that remains in the heart and great vessels after the surgical procedure has been completed. Trapped air can result in the development of an air embolism. The injury produced by an air embolism can vary from symptoms that are not clinically detectable to stroke or death due to a massive embolism.

Therefore, it is an object of the invention to provide a system that will prevent or minimize the occurrence of an air embolism during cardiovascular surgery. Another object is to provide a system that can be used to remove trapped air from the heart in both conventional open heart surgery and "minimally invasive" surgeries in which a small surgical incision is used.

SUMMARY OF THE INVENTION

These and other objects are achieved by the present invention which is directed to a system and method for preventing the development of an air embolism in the brain or other part of an animal from an open heart surgical procedure. Also provided is a device that can accurately control the pressure and/or flow of gas into the heart cavity and/or blood vessels.

The system is composed of a gas source (e.g., carbon dioxide ($CO_2$)) that can be infused into the body to inhibit or prevent air from entering into the heart and great vessels and to dislodge and remove air bubbles, a mechanism for controlling pressure and flow of carbon dioxide through the system and into the heart chamber or blood vessels, and a tube that is inserted into the heart chamber for conveying the carbon dioxide thereinto. The carbon dioxide ($CO_2$) source, the pressure/flow controlling mechanism, and the carbon dioxide ($CO_2$) conveying tube are in fluid communication with each other. The pressure/flow controlling mechanism is positioned between the $CO_2$ source and the $CO_2$ conveying tube, and provides a flow of the carbon dioxide through the system and into the heart at a pressure and flow rate as desired during the surgical procedure. The system preferably includes a bacterial filter for removing microorganisms from the carbon dioxide prior to entry into the heart chamber, that is preferably disposed between the pressure/flow controlling mechanism and the $CO_2$ conveying tube.

The system can be used in an open heart surgical procedure such as an aortic valve or mitral valve replacement or a surgery on a great vessel to prevent the development of an air embolism in the brain of the animal. The $CO_2$ conveying tube of the system is inserted into the heart or great vessel, carbon dioxide is infused at a pressure and flow to effectively prevent air ($N_2$) from entering the body cavity and to maintain it filled with the $CO_2$, and/or to purge air and air bubbles out of the cavity. Preferably, the $CO_2$ conveying tube includes a plurality of apertures for flowing the carbon dioxide therethrough into the body cavity. The $CO_2$ conveying tube can be inserted prior to or during the surgical procedure, or after the surgical procedure has been completed. Optionally, the purged air and $CO_2$ can be actively removed using an aspirator inserted into a vent opening. This infusion of carbon dioxide and removal of air through the vent opening removes dangerous air bubbles that can subsequently enter the arteries and cause an embolism in the animal.

The system can also include a tube for removing blood, foamed blood and other fluid from the body cavity (e.g., heart). The fluid removal tube, or "sump," can be connected to a conventional heart-lung machine or other device or mechanism that will operate to draw the fluid through the fluid removal tube and out of the body cavity. A device such as a heart-lung machine can be used to treat the blood to remove the carbon dioxide and dissolved gases and add oxygen, and then return the treated blood into the body of the animal.

The $CO_2$ conveying tube and other fluid conveying tube(s) can be separate tubes or combined as a single tube having a multiple lumen. In a multiple lumen tube, it is preferred that the $CO_2$ conveying tube and the fluid conveying tube(s) are parallely arranged.

The system can be used in conjunction with devices to monitor the amount of undissolved gas bubbles in the body. The percentage of air or nitrogen and carbon dioxide in the aspirated gas can be determined using conventional monitoring devices. A trans-esophagus ultrasonic imaging device can be used prior to and after the surgical procedure to image the heart and the aorta and monitor the presence of gas bubbles. A transcutaneous ultrasonic imager can be used to detect gas bubbles going through the carotid arteries.

An example of the use of the present system is in an open heart surgery to replace the aortic valve. In such an application, the $CO_2$ conveying tube can be inserted into the left ventricle and the pressure/flow controlling mechanism is set to deliver the carbon dioxide at a low pressure effective to prevent air from entering the left heart and maintain it filled with the $CO_2$, preferably at about 5–20 mmHg. In the case where air has entered the heart, a higher pressure can be used to purge air bubbles trapped in the left heart and the aorta, preferably at about 30–100 mmHg. A vent or opening can be provided in the aorta to allow for the escape of air and air/$CO_2$ mixture. An aspirating device (e.g., tube) can be inserted through the opening to mechanically and actively remove the displaced and purged air. A fluid removing tube can be inserted into the left heart to facilitate the removal of blood (including blood that is foamed with gas bubbles) so that the blood volume within the left heart is reduced and the surgical site is kept clear during surgery.

After the heart valve replacement or other surgery is completed, the pressure and flow of the carbon dioxide into the left ventricle can be reduced, preferably to about 5–20 mmHg, to maintain the left heart and aorta filled with carbon dioxide. The portion of the left heart and great vessels that is not occupied by blood is filled with $CO_2$ (rather than air), with blood entering the left heart from the pulmonary vein. The $CO_2$ conveying tube and the fluid removing tube can then be removed from the left heart.

As the left heart is filling with blood, the carbon dioxide can be administered at either a low pressure or a high pressure depending on the presence or absence of air in the left heart and the need to dispel the air bubbles from the chamber. Carbon dioxide can be delivered at a higher pressure mode while the surgical wound is open, or at low pressure when the wound is sutured closed.

Where use of the system is delayed until after completing the surgery, the $CO_2$ conveying tube and the fluid removing tube of the system are inserted through the surgical wound or another opening into the left heart, and the carbon dioxide is preferably delivered at a high pressure to purge the air and air bubbles out of the heart and aorta through the venting hole. Blood, particularly foamed blood, can be removed from the left heart via the fluid removing tube. The flow and pressure of the carbon dioxide can then be reduced to maintain carbon dioxide in the left heart and aorta as it fills with blood, and the tubes can then be removed from the body.

Advantageously, the use of the present system can be easily incorporated into any type of open heart surgical procedure. The system is simple to use and provides a high level of reliance in preventing the forming and in removing air bubbles from the heart to effectively prevent the occurrence of air embolisms. The system is also a time-saver for operating personnel by replacing the current procedures for removing air bubbles from the heart after a surgery that are difficult, unreliable and time-consuming. The present system can advantageously be used in minimally invasive open heart surgeries that utilize a small surgical incision and do not allow the extensive heart manipulation used in traditional methods to expel trapped air from the heart. Cardiovascular surgeries other than heart valve replacement such as surgeries on the great vessels can also be benefited by the use of the present system to prevent air embolism.

BRIEF DESCRIPTION OF THE DRAWINGS

Throughout the following views, reference numerals will be used in the drawings, and like reference numerals will be used throughout the several views and in the description to indicate corresponding parts of the invention.

DETAILED DESCRIPTION OF THE INVENTION

Figure 1:
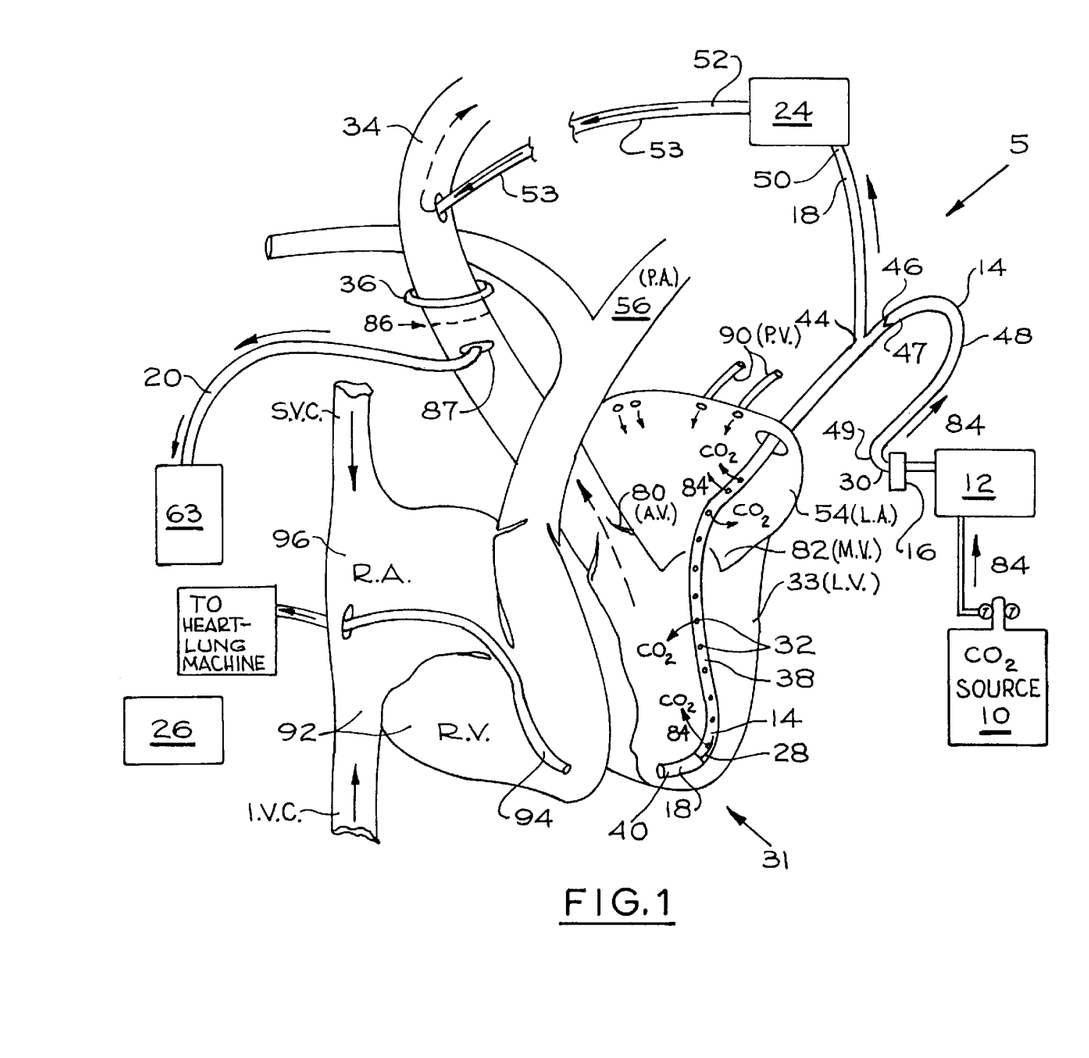
FIG. 1 is an illustration of the system of the invention in use in a cardiovascular surgery.

The present system for preventing an air embolism in a cardiovascular surgery involves supplying carbon dioxide into the heart at controlled low pressures and/or flow rates to prevent the entrance of air into the heart and great vessels during all phases of cardiac and great vessel surgery, and/or to displace air at the late phase of the surgery. As used herein, the term "great vessels" includes the aorta, the heart arteries, the carotid arteries, the axillary arteries and pulmonary veins. The term "surgical wound" means the surgical incision made on the heart and great vessels for the purpose of performing the surgery. The abbreviations in FIG. 1 are as follows: R.V.=right ventricle, L.V.=left ventricle, R.A.=right atrium, L.A.=left atrium, P.A.=pulmonary artery, P.V.=pulmonary veins, I.V.C.=inferior vena cava, S.V.C.=superior vena cava, A.V.=aortic valve, and M.V.=mitral valve.

The nitrogen in air is very insoluble and if a bubble of air is large enough to block a vessel supplying the central nervous system, it can remain blocked for a period of time and cause irreversible damage. The ratio of absorption coefficients in water $\alpha\ CO_2 / \alpha\ N_2$ is shown below.

| 0° C. | 10° C. | 20° C. | 37° C. |
|---|---|---|---|
| 73 | 64 | 57 | 46 |

In water, carbon dioxide is about 57 times as soluble as nitrogen ($N_2$) at 20° C. and about 46 times as soluble at 37° C. In addition, carbon dioxide ($CO_2$) is over 53% heavier than air and about 58% heavier than nitrogen. Therefore, the infusion of carbon dioxide into the left heart can be used to effectively prevent air from entering the left heart or aorta through a surgical incision, or if air has already entered the heart or aorta, the infusion of carbon dioxide can displace air upward (through the aorta and left atrium). The air then either escapes through an incision or can be aspirated by an aspirator tube inserted into the aorta or left atrium.

A system according to the invention, designated generally with the numeral 5, is illustrated in FIG. 1. The system 5 is composed of a source 10 of carbon dioxide ($CO_2$) that can effectively be infused into the body organ for displacement or removal of air and air bubbles, a carbon dioxide ($CO_2$) pressure and flow controlling mechanism 12, and a carbon dioxide ($CO_2$) infusion or conveying tube 14, all of which are in fluid communication. For the purposes of explanation, the use of carbon dioxide ($CO_2$) as a specific gas is described herein. However, other similar gases can be effectively used in the present system in place of carbon dioxide to dispense air and air bubbles in the heart and vessels. Therefore, as used herein, the terms "$CO_2$" source, "$CO_2$" pressure and flow controlling mechanism, "$CO_2$" infusion/conveying tube, and the like, are meant to relate to like devices used with other related gases in accordance with the present system.

Preferably, the system 5 further includes a bacterial filter 16 positioned between the pressure/flow controlling mechanism 12 and the $CO_2$ conveying tube 14 to filter out bacteria, fungi, and other microorganisms from entering the heart cavity. The system 5 can also include a tube 18 for removing fluid, and a tube 20 for aspirating air/gas. The system 5 can further include a heart-lung machine 24 or other like mechanism to actively remove and/or process the removed blood, and an ultra-sound imaging machine 26 to detect undissolved gas bubbles in the heart and aorta.

The $CO_2$ conveying tube 14 includes a first end 28 and a second end 30. When using the system 5 in an open-heart surgery as depicted in FIG. 1, the first end 28 of the $CO_2$ conveying tube 14 is placed into the heart 31 and is composed of a plurality of apertures 32 for delivery of $CO_2$ therethrough. The other (second) end 30 of the $CO_2$ conveying tube 14 is adapted for connection to the bacterial filter 16 connected to the pressure/flow controlling mechanism 12 that is in turn connected to the $CO_2$ source 10. The fluid removal tube 18 is used for transporting blood from the left ventricle 33 to a heart-lung machine 24 that will treat the blood (e.g., remove gases and add oxygen), and then return the blood into the aorta 34 above a clamp 36 that has been placed on the aorta 34 to block the flow of blood therethrough. Clamp 36 may be an external clamp or an internal liquid balloon clamp.

Figure 2:
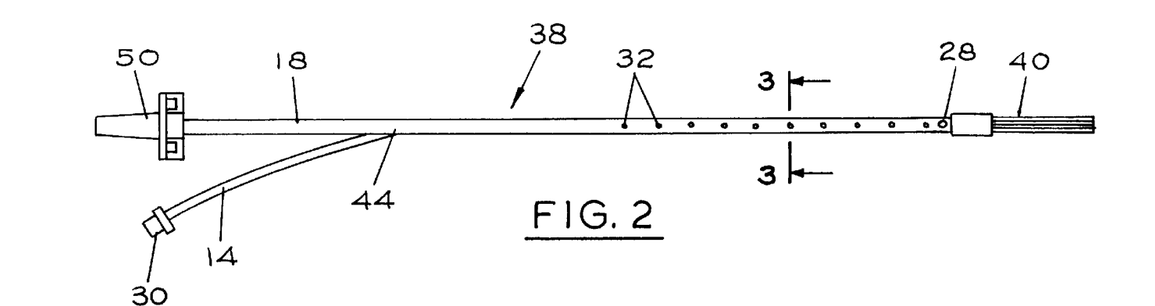
FIG. 2 is a side view of a double lumen tubing composed of the carbon dioxide ($CO_2$) conveying tube and the fluid removal tube.
Figures 3, 4:
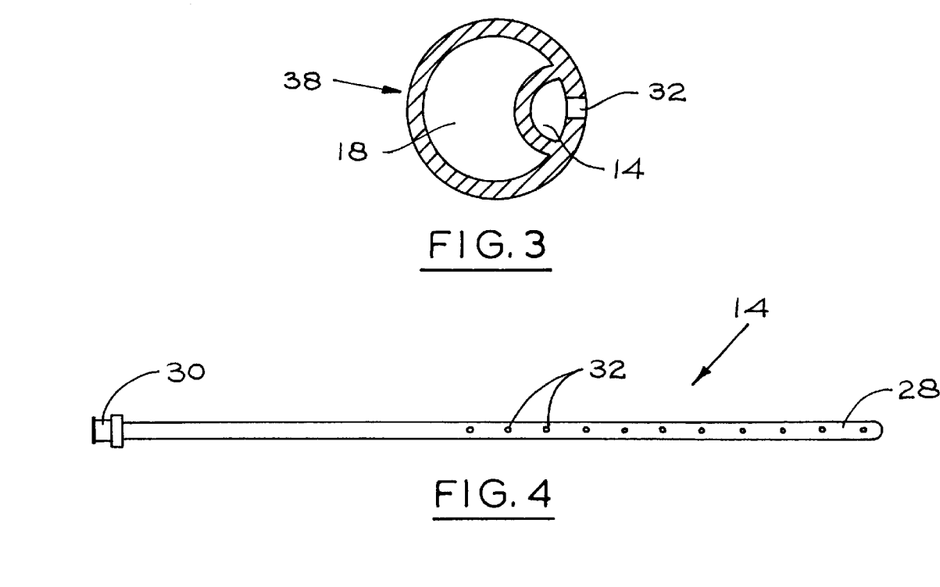
FIG. 3 is a cross-sectional view of the tubing of FIG. 2 along lines 3—3.
FIG. 4 is a side view of a single carbon dioxide ($CO_2$) conveying tube.

As shown in FIGS. 1–3, the fluid removal tube 18 and the $CO_2$ conveying tube 14 can be combined into a single, double lumen tube 38. As shown in cross-sectional view in FIG. 3, the double lumen tube 38 has two channels defining the fluid removal tube 18 and the $CO_2$ conveying tube 14 which, as shown, has a smaller inside diameter. The open first end 40 of the fluid removal (sump) tube 18 extends beyond the first end (tip) 28 of the $CO_2$ conveying tubing 14. As shown, the apertured $CO_2$ conveying tube 14 of the double lumen tube 38 is terminated with a slanted open (first) end 28 that is about 1–2" shorter than the first end 40 of the fluid removal tube 18.

Starting from the first end 28 of the $CO_2$ conveying tube 14, there is a series of side aperture openings 32 leading into the channel of the $CO_2$ conveying tube portion 14 that allows for the passage of carbon dioxide into the left heart 31. Preferably, the apertures 32 are of sufficient size and present negligible flow resistance. The second (proximal) end 44 of the double lumen tube 38 splits into a separate fluid removal tube 18 and a separate $CO_2$ conveying tube 14. Referring to FIG. 1, the second (proximal) end 30 of the $CO_2$ conveying tube 14 is connectable to the pressure/flow controlling mechanism 12, preferably through a bacterial filter 16. Preferably, as shown, the second (proximal) end 30 of the $CO_2$ conveying tube 14 is connected to the pressure/flow controlling mechanism 12 through an in-line check valve 46 to a first (distal) end 47 of an about eight (8) foot long tubing 48 having a central bore for conveying carbon dioxide therethrough, preferably with an inside diameter of at least about 3/16", with the second (proximal) end 49 of the 8-foot tubing 48 connected to a bacterial filter 16 that, in turn, is connected to the pressure/flow controlling mechanism 12.

The second (proximal) end 50 of the fluid removal tube 18 is adapted for connection to a mechanism for actively removing and clearing the blood from the left heart 31 or other surgical site, and/or for processing fluid and blood removed from the heart chamber. As depicted in FIG. 1, the fluid removal tube 18 is connected to a heart/lung machine 24 which conventionally incorporates a roller-type pump or a centrifuge pump to remove blood at a controlled rate. The heart/lung machine 24 can be attached to tubing 52 for return of the processed blood to the aorta 34 in the direction of arrows 53.

Figure 5:
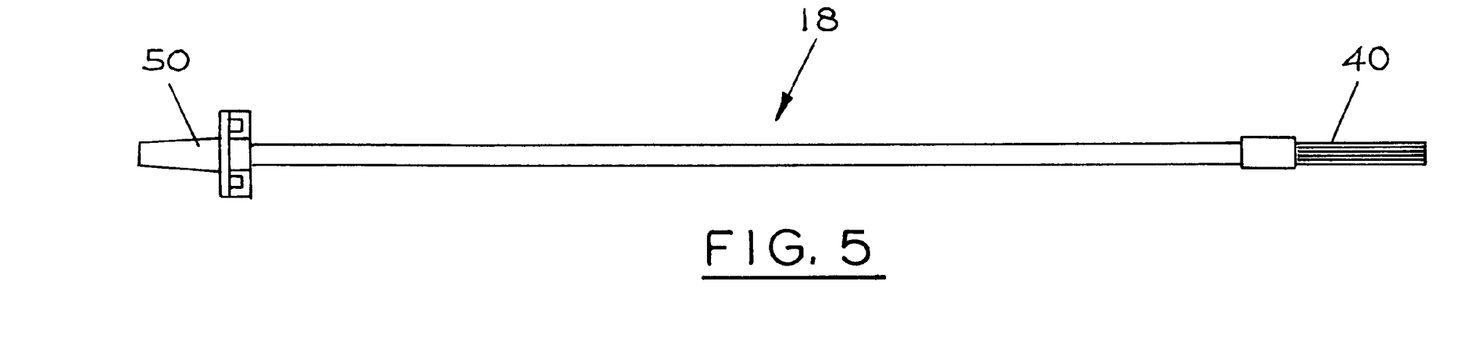
FIG. 5 is a side view of a single fluid removal tube.

In another embodiment as shown in FIGS. 4 and 5, the $CO_2$ conveying tube 14 and fluid removal tube 18 can be separate tubes. The separate, single lumen $CO_2$ conveying (infusion) tube 14 can be placed in the left ventricle 33 or left atrium 54, and a separate, single lumen fluid removal tube (sump line) 18 can be inserted into the left ventricle 33, as shown, or placed in the pulmonary artery 56. The $CO_2$ conveying (infusion) tube 14 includes a first end 28 that is placed into the left ventricle 33 with side apertures 32 for infusion of $CO_2$ into the left heart, and a second end 30 that is connectable to the pressure/flow controlling mechanism (console) 12 preferably through an in-line check valve 46, the tubing 48, and the bacterial filter 16 (see FIG. 1). Referring to FIG. 5, the singular fluid removing tube 18 includes a first end 40 for placement in the left heart 31 (or pulmonary artery 56) and a second end 50 for attachment to a fluid pump or, as shown in FIG. 1, the heart-lung machine 24.

Figure 6:
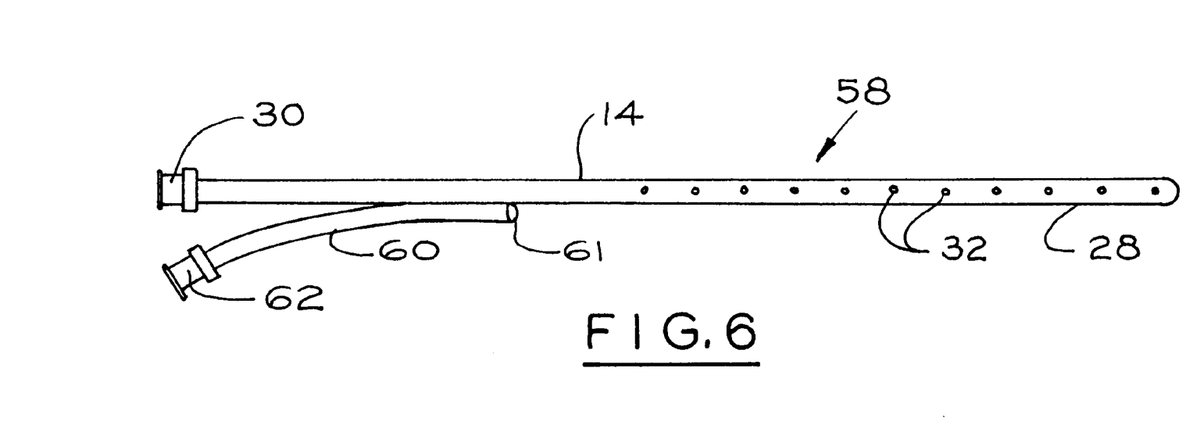
FIG. 6 is a side view of a carbon dioxide ($CO_2$) infusion/air exchange tubing.

Also useful is a double lumen $CO_2$ (infusion) conveying/air exchange tubing 58 with uneven tip ends, as illustrated in FIG. 6. As shown, the longer $CO_2$ conveying tubing 14 includes side apertures 32 in the first (tip) end 28 for $CO_2$ infusion, and the shorter air exchange tubing 60 has an open first end 61 for removing air and/or an air/$CO_2$ mixture from the heart 31. In use, the double lumen tubing 58 is placed such that the first end 28 of the $CO_2$ conveying (infusion) line 14 is positioned in the lower portion of the left heart 31 for infusion of carbon dioxide thereinto, and the open first end 61 of the shorter air exchange tube 60 is placed just inside the surgical incision of the left heart 31 or aorta 34 for removing air or an air/$CO_2$ mixture from the heart cavities. In this case, a separate fluid removal tube 18 as depicted in FIG. 5 can be used with the first (tip) end 40 placed into the lower part of the left ventricle 33 for removal of blood (and foamed blood). The second end 30 of the $CO_2$ conveying tube 14 is connectable to the $CO_2$ pressure/flow controller 12, and the second end 62 of the air exchange tube 60 is connectable to an aspiration source 63.

The pressure/flow controlling mechanism 12 is positioned between the $CO_2$ source 10 and the $CO_2$ conveying tube 14 and provides a flow of the carbon dioxide through the system 5 and into the left heart 31 at a flow rate as desired during the surgical procedure. An example of a pressure/flow controlling mechanism 12 is the console illustrated in FIG. 7. The console 12 provides carbon dioxide ($CO_2$) at a desirable (High or Low) flow rate that can be selected by the operator. Preferably, the controlling mechanism 12 is capable of supporting a $CO_2$ flow rate of up to about 1000 ml/min at the High flow mode and about 200 ml/min at the Low flow mode. It is also preferred that the output pressure is automatically limited to about 5–20 mmHg at a Normal flow and can be raised to 35 to 100 mmHg when used to purge out air. The control console 12 is simple to operate and can be easily managed by a perfusionist.

Figure 7:
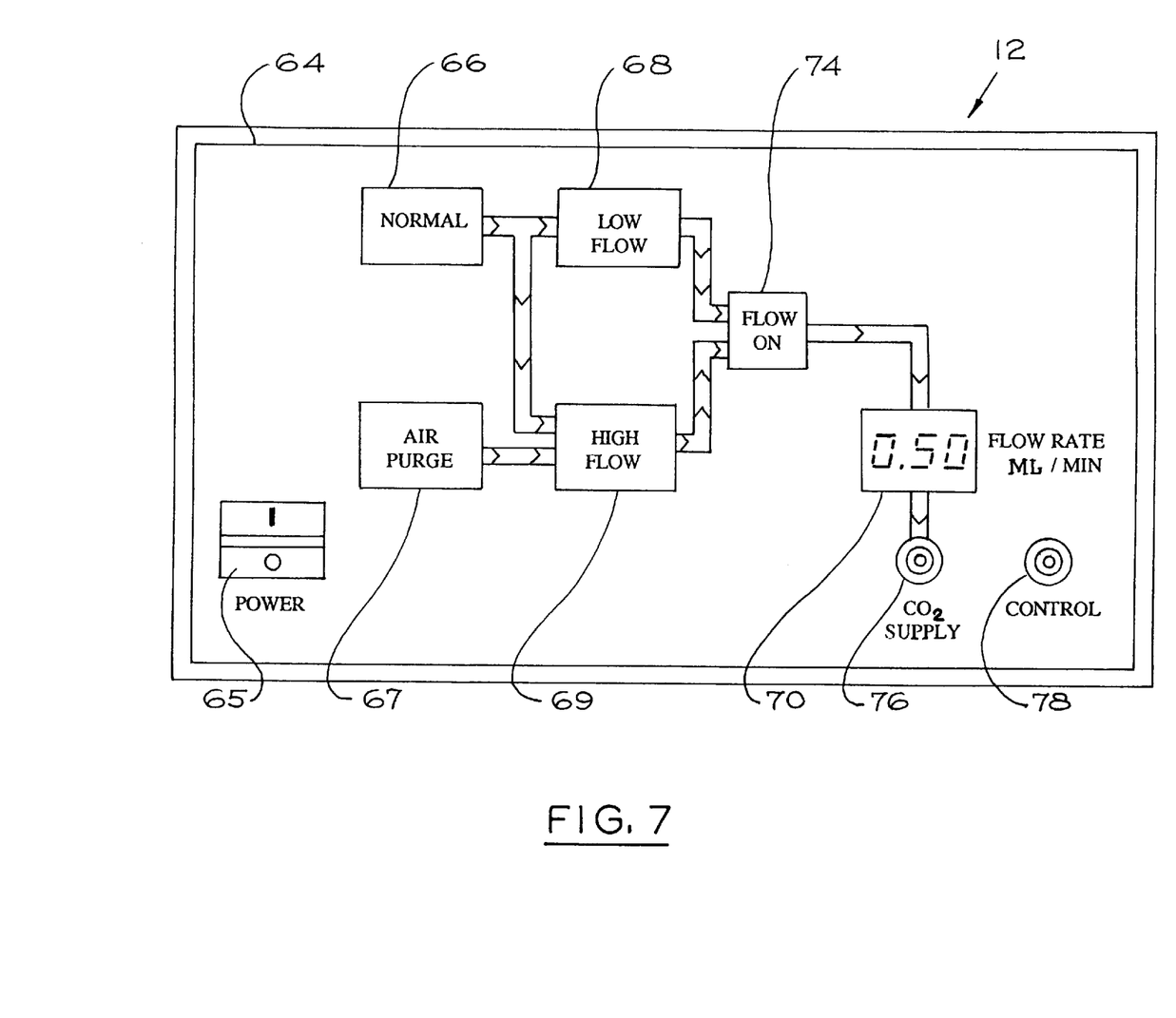
FIG. 7 is a front view of a console for controlling the pressure and flow of carbon dioxide ($CO_2$)

As illustrated in FIG. 7, the mechanism 12 is composed of a console 64 with various controls and indicators, including: a power switch 65; control knobs 66 and 67 to select between "Normal" and "Air Purge" modes, respectively; control knobs 68 and 69 to select between "Low" and "High" flow in the Normal mode, respectively; a display 70, preferably digital, showing the actual $CO_2$ flow rate in l/min; a "flow" control knob 74 to activate and deactivate the $CO_2$ supply; a male lure lock connector 76 for $CO_2$ output; and a male lure lock connector 78 for pressure feedback control. Preferably, the control knobs are push buttons and are illuminated when activated.

When the control knob 66 for "Normal" mode is set, the maximum pressure in the heart is limited to a pre-selected low level, preferably about 5–20 mmHg. When the mechanism 12 is set to "Air Purge" mode (control knob 67), a limit of a pre-selected high pressure is imposed, preferably about 35–100 mmHg. In the Normal mode, setting the control knob 68 for "Low" flow will supply a flow rate of a low pre-selected flow rate, for example, about 0.2 l/min. Setting the control knob 69 for "High" flow will supply a flow rate of a high pre-selected flow rate, for example, about 1 l/min. The flow rates are maintained unless the pressure in the heart exceeds the pressure limit that has been selected.

As illustrated in FIG. 1, an ultra-sound imaging machine 26, as known and used in the art, can be used to monitor the amount of undissolved gas bubbles in the body. For example, the ultra-sound imaging machine 26 can have a trans-esophagal head to monitor gas bubbles in the heart and the aorta and display the image on the console screen prior to and after the surgical procedure, or a transcutaneous head to image gas bubbles within the carotid arteries. Blood $PO_2$ and $PCO_2$ can be monitored with the use of a separate device according to known methods.

The present system 5 can be used in conjunction with a cardiovascular surgical procedure to prevent the development of an air embolism in the body of the animal. For example, as illustrated in FIG. 1, the system 5 can be used in a surgery to replace the aortic valve 80. As shown, a double lumen tube 38 composed of the $CO_2$ conveying tube 14 and the fluid removal tube 18 is inserted through the left atrium 54, through the mitral valve 82, and into the lower area of the left ventricle 33 for $CO_2$ infusion and blood removal. The second ends 30, 50 of the $CO_2$ conveying tube 14 and the fluid removal tube 18, respectively, are connected to the pressure/flow controlling mechanism 12 and the heart-lung machine 24, respectively.

Referring to FIG. 1, carbon dioxide from the $CO_2$ source 10 is conveyed in the direction of the arrows 84 through the pressure/flow controlling mechanism 12, the bacterial filter 16, and the $CO_2$ conveying tube 14, the check valve 46, and the apertures 32 into the left ventricle 33. The rate of flow of carbon dioxide into the left heart 31 at low pressure is controlled to be higher than the rate that carbon dioxide is being dissolved in the blood so that the left heart chambers 33, 54 and the open portion of the aorta 34 that are not filled with blood, are filled with carbon dioxide. The presence of $CO_2$ which is heavier than air, will effectively prevent air from entering into the chambers and aorta.

At the completion of the valve replacement, the bulk of the $CO_2$ is forced out by the blood refilling the heart before the surgical wound, the wound 86, and the wound to administer cardioplegia 87, are closed. Remaining small $CO_2$ bubbles dissolve relatively quickly.

In applications in which a $CO_2$ conveying tube 38 is not used, or in other instances where the heart cavity contains a significant amount of air at the completion of the valve replacement procedure, the rate of fluid removal is increased until all fluids (and foam, if any) are removed from the left heart while the carbon dioxide flow is increased by adjusting the console 12 to the air purge mode. After the heart 31 has been purged of air by the infusion of carbon dioxide for a period of about 1–2 minutes, while the surgical wound (incision) 86 and/or the cardioplegia opening 87 of the aorta 34 are open or partially open to allow the $CO_2$/air mixture to escape.

This process can be enhanced by placing an aspirator tubing 20 through the incision 86 or opening 87 into the lumen of the aorta 34 to actively remove the $CO_2$/air mixture. The aspiration is stopped after a short period of time (about 1–2 minutes), and the left heart 31 is allowed to fill with blood from the pulmonary veins 90. The blood will displace the bulk of the carbon dioxide now in the heart and aorta (evident from the outflow being substantially all blood and the ultrasound imager not showing a significant number of gas bubbles in the left heart chambers 33, 54). The $CO_2$ conveying tubing 14 (or double lumen tube 38) is withdrawn from the left heart 31. Any remaining $CO_2$ bubbles can be monitored by the ultrasound imager 26 to ensure that they have escaped or dissolved before closing the aortic wound 87 and opening the aortic clamp 36 to restart the normal heart/lung circulation.

Figure 8:
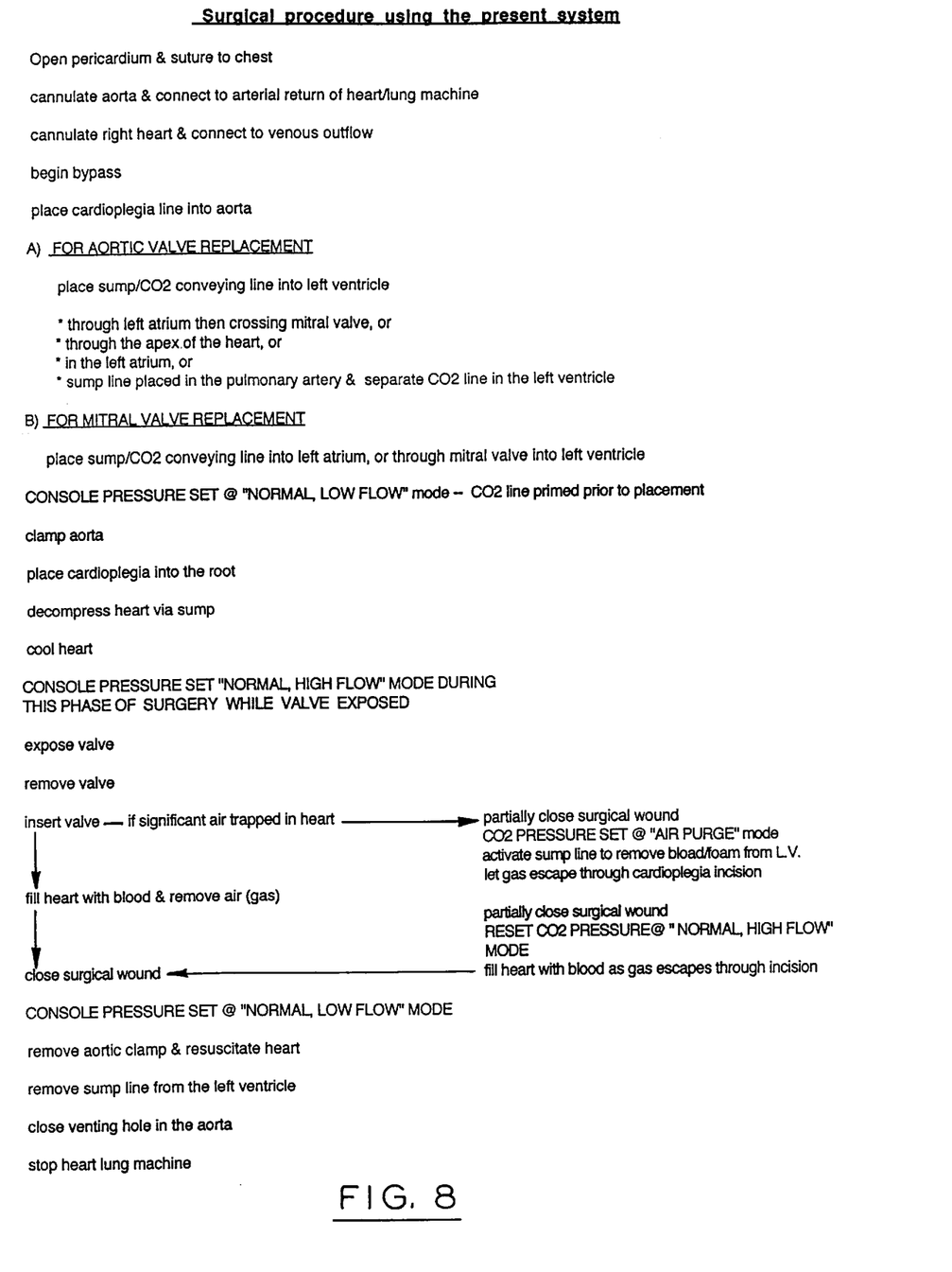
FIG. 8 is a diagram outlining a conventional surgical procedure using the present system.
Figure 9:
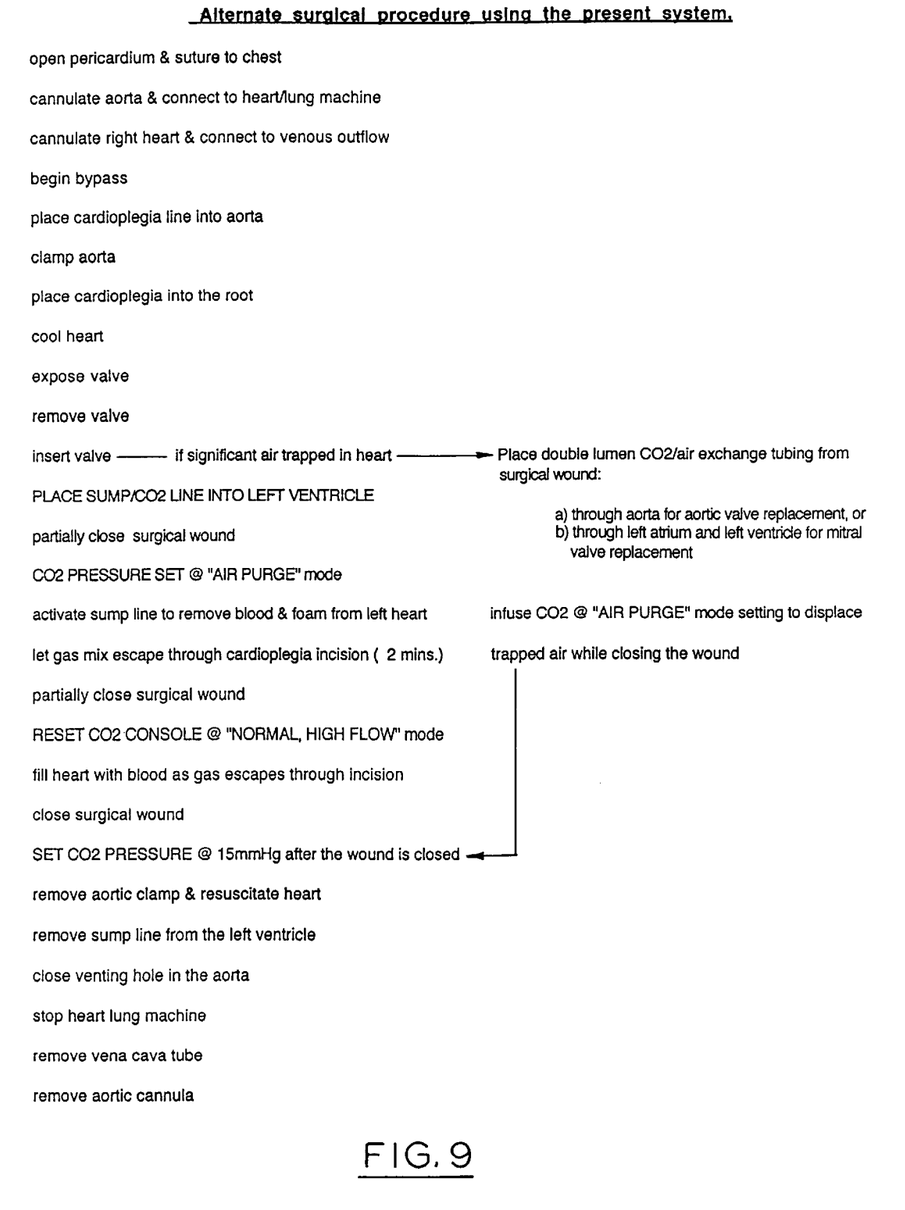
FIG. 9 is a diagram outlining a conventional surgical procedure using the present system in another manner.

Examples of open heart surgical procedures using the present system 5 in an aortic valve replacement are illustrated in FIGS. 8 and 9. For example, as illustrated in FIG. 8, after the pericardium is opened and sutured to the chest, the surgical procedure (I) would include the following steps.

1) cannulate the aorta 34 and connect the cannula (tubing) 52 to the arterial return of the heart/lung machine 24;

2) cannulate the right heart 92 and connect the cannula 94 to the venous outflow of the heart/lung machine 24;

3) begin the bypass procedure;

4) place the cardioplegia line (not shown) through aortic incision 87 into the lumen of the aorta 34;

5) place the fluid removal (sump)/$CO_2$ conveying tube 38 (double lumen) into the left ventricle (L.V.) 33:

a) through the left atrium (L.A.) 54 then crossing the mitral valve (M.V.) 82;

b) through the apex of the heart, or c) into the left atrium 54, or d) if separate tubes are used, place the fluid removal (sump) line 18 in the pulmonary artery (P.A.) 56, and a separate $CO_2$ conveying tube 14 in the left ventricle (L.V.) 33;

6) set the pressure of the pressure/flow controlling mechanism (console) 12 to "Normal" 66 and "Low flow" 68 modes ($CO_2$ conveying tube line 14 primed prior to placement);

7) place a clamp 36 onto the aorta 34;

8) place the cardioplegia line (not shown) into the root;

9) decompress the heart via the fluid removal (sump) line 18;

10) cool the heart;

11) set the $CO_2$ console 12 to the "Normal" 66, and "High flow" 69 modes;

12) expose the aortic valve 80;

13) remove the valve 80;

14) insert the replacement valve 80;

15) fill the left heart 31 with blood and remove the air (gas);

16) close the surgical wound;

17) set the console 12 to the "Normal" 66 and "Low flow" 68 modes after the wound is closed;

18) remove the aortic clamp 36 and resuscitate the heart;

19) remove the fluid removal (sump) $CO_2$ conveying tube 38 from the left ventricle 33;

20) close the venting hole 87 in the aorta 34;

21) stop the heart-lung machine 24;

22) remove the vena cava tubing (not shown); and 23) remove the aortic cannula 94.

Alternatively, in cases of significant air trapped in the heart caused by substantial vacuum suction used during the removal and insertion of the valve (steps 13 and 14, above), the procedure can be modified as follows. After insertion of the valve (step 14), the modified procedure (II) would include the following steps:

15a) partially close the surgical wound;

16a) set the $CO_2$ console 12 to the "Air Purge" mode 67 to displace trapped air from the left heart 31;

17a) activate the fluid removal (sump) line 38 until the remaining blood and foam, if any, in the left ventricle 33 are removed while letting the gas mixture escape through the cardioplegia incision 87 and partially closed surgical wound (about two minutes);

18a) reset the $CO_2$ console 12 to the "Normal" 66, "High flow" 69 modes;

19a) fill the heart with blood while letting the gas mixture escape through the cardioplegia incision 87;

The modified procedure (II) would then proceed through the remaining steps of the above-described general procedure (I) starting at step 16 ("close the surgical wound").

Another surgical procedure (III) is illustrated in FIG. 9, in which the system is not used until at the end of the surgical procedure (e.g., after insertion of the valve) to remove air trapped in the heart. In such cases, the general procedure (I) can be modified as follows. After insertion of the replacement valve (step 14 of general procedure (I), above), place the fluid conveying (sump)/$CO_2$ conveying tube 38 into the left ventricle 33 of the heart 31, and proceed through steps 15a–19a of the modified procedure (II), followed by steps 16–23 of the general procedure (I). Preferably, a double lumen $CO_2$/air exchange tube 38 is used that is composed of a $CO_2$ conveying tube 14 and fluid removal tube 18 with uneven tip ends 28, 40, respectively. The double lumen exchange tubing 38 can be inserted through the surgical wound and the aorta in cases of an aortic valve replacement, and through the left atrium and left ventricle for a mitral valve replacement.

The system 5 can also be used in a mitral valve replacement. To do so, the general procedure (I) described above can be followed, except that step 5 would be modified by placing the fluid removal (sump)/$CO_2$ conveying tube 38 through a surgical incision of the left atrium 54 or an incision of the superior pulmonary vein 90. The tube 38 can be placed into the left atrium 54 or, in some cases, through the mitral valve 82 into the left ventricle 33. It is desirable that apertures 32 extend the full length of the section of $CO_2$ tubing 38 that is inside the heart so that all spaces in the heart cavities, the pulmonary veins and the aorta that are not occupied by fluid, are filled with carbon dioxide ($CO_2$). In the case that the surgical site is accessed through an incision of the right atrium 96, and an opening of the septum, it is preferred that the tubing 38 is placed through the same pathway. In a mitral valve replacement, more interconnected cavities may be exposed to air. Therefore, the tubing 38 is placed in such a way that carbon dioxide ($CO_2$) will flow in and occupy any space where air would otherwise occupy.

The system 5 can also be used in a minimally invasive cardiac procedure. In that case, the $CO_2$ conveying tube 14 can be integrated with a balloon endoaortic catheter (not shown) which includes a venting cannula, and cannula for delivering cardioplegia. In such an application, carbon dioxide ($CO_2$) can be delivered through one of the cannulas of the catheter. Alternatively, a cannula or tube 14 can be integrated with the balloon catheter device.

The present system for preventing development of an air embolism in an animal can be used in cardiovascular surgeries other than heart valve replacement, for example, a surgery on the aorta, the arteries of the heart, the carotid arteries, the axillary arteries, the pulmonary veins, and other great vessels. In such an application, the fluid removal tube and the $CO_2$ conveying tube (18, 14, or 38) are placed appropriately to prevent air entering into the vessels. Carbon dioxide can be also infused in to displace air trapped in the vessels.

The invention has been described by reference to detailed examples and methodologies. These examples are not meant to limit the scope of the invention. It should be understood that variations and modifications may be made while remaining within the spirit and scope of the invention, and the invention is not to be construed as limited to the specific embodiments shown in the drawings. The disclosures of the cited references are incorporated by reference herein.

What is claimed:

1. A system for preventing an air embolism in the brain of an animal in a cardiovascular surgical procedure, comprising:
  a) a source of a gas;
  b) a mechanism for controlling pressure and flow of the gas therethrough, having an inlet end and an outlet end, the inlet end being connected to the gas source; and
  c) a tube for conveying the gas therethrough having a first end and a second end, and a member for preventing blood from flowing from the heart into the gas conveying tube; the first end adapted for placement in the heart of the animal and having a plurality of apertures for passage of the gas therethrough into the heart;

wherein the pressure/flow controlling mechanism is disposed between the gas source and the gas conveying tube; and the gas source, the pressure/flow controlling mechanism and the gas conveying tube are in fluid flowing communication for conveying the gas therethrough;

and the pressure/flow controlling mechanism is operable to provide a flow of the gas through the system such that when the first end of the gas conveying tube is placed into the heart, the pressure and flow of the gas from the pressure/flow controlling mechanism through the gas conveying tube into the heart is effective to inhibit air from entering the heart, great vessel, or both, or to remove air from the heart, the great vessel, or both.

2. The system according to claim 1, further comprising:
  a tube for removing fluid from the heart, having a first end, a second end, and a central channel, wherein the second end of the fluid removal tube is connectable to a mechanism operable to draw the fluid out of the heart and through the central channel of the fluid removal tube.

3. The system according to claim 2, wherein the fluid removal mechanism is a heart-lung machine comprising a pump mechanism.

4. The system according to claim 2, wherein the gas conveying tube and the fluid conducting tube are separate lumens of a multiple lumen tube.

5. The system according to claim 4, wherein the gas conveying tube and the fluid conducting tube are parallely arranged.

6. The system according to claim 1, wherein the gas is carbon dioxide.

7. The system according to claim 1, further comprising:
  a mechanism for aspirating air having an inlet end; and
  a tube for conveying air therethrough having a first end and a second end, the first end of the air conveying tube being connected to the inlet end of the air aspirating mechanism and the second end being insertable into the body of the animal.

8. The system according to claim 1, wherein the pressure/flow controlling mechanism is operable to provide a low flow pressure of the gas of about 5–20 mmHg into the heart to effectively prevent air entering into the heart and maintain the heart filled with the gas, and a high pressure of about 30–100 mmHg to effectively purge air from the heart.

9. The system according to claim 1, wherein the gas conveying tube is defined by a first lumen of a double lumen tube, and a second lumen of the double lumen tube defines an air exchange tube for removing gas from the heart having a first end with an opening and a second end adapted for connection to an aspiration source; the gas conveying tube having a length greater than the air exchange tube such that when the double lumen tube is inserted through an incision of the left heart or aorta and the first end of the gas conveying tube is positioned in the lower portion of the left heart, the first end of the air exchange tube is positioned in the heart in proximity to the incision.

10. The system according to claim 1, wherein the gas conveying tube is integrated with a balloon endoaortic catheter.

11. A system for preventing an air embolism in the brain of an animal in a cardiovascular surgical procedure, comprising:

a) a source of a gas;
b) a mechanism for controlling pressure and flow of the gas therethrough, having an inlet end and an outlet end, the inlet end being connected to the gas source;
c) a tube for conveying the gas therethrough having a first end and a second end, the first end adapted for placement in the heart of the animal and having a plurality of apertures for passage of the gas therethrough into the heart; and
d) a filter for removing microorganisms disposed between the pressure/flow controlling mechanism and the gas conveying tube, having an inlet end connected to the outlet end of the pressure/flow controlling mechanism for receiving the gas into the filter, and an outlet end connected to the second end of the gas conveying tube for passing the filtered gas thereinto,
wherein the pressure/flow controlling mechanism is disposed between the gas source and the gas conveying tube; and the gas source, the pressure/flow controlling mechanism and the gas conveying tube are in fluid flowing communication for conveying the gas therethrough;
and the pressure/flow controlling mechanism is operable to provide a flow of the gas through the system such that when the first end of the gas conveying tube is placed into the heart, the pressure and flow of the gas from the pressure/flow controlling mechanism through the gas conveying tube into the heart is effective to inhibit air from entering the heart great vessel or both or to remove air from the heart, the great vessel, or both.

12. The system according to claim 11, wherein the gas conveying tube comprises a member for preventing blood from flowing from the heart into the gas conveying tube.

13. A system for preventing an air embolism in an animal in an cardiovascular surgical procedure, comprising:
a source of carbon dioxide in fluid communication with a tube insertable into the heart for conveying the carbon dioxide thereto, having disposed thereinbetween a mechanism for controlling pressure and flow of carbon dioxide therethrough; the carbon dioxide conveying tube having a first end and a second end, and a member for preventing blood from flowing from the heart into the carbon dioxide conveying tube; the first end adapted for placement in the heart of the animal and having a plurality of apertures for passage of carbon dioxide therethrough; and the second end adapted for connection to the pressure and flow controlling mechanism;
wherein the pressure/flow controlling mechanism is operable to conduct the carbon dioxide into the heart through the carbon dioxide conveying tube at a pressure effective to eliminate air bubbles from the heart during the surgical procedure, after completion of the surgical procedure, or both.

14. An assembly for use in a cardiovascular surgical procedure for preventing an air embolism in the brain of an animal, comprising, in combination:
a) a mechanism for controlling pressure and flow of gas therethrough, having an inlet end and an outlet end; the inlet end adapted for connection to a source of the gas;
b) a filter for removing microorganisms, having an inlet end and an outlet end; the inlet end adapted for connection to the outlet end of the gas pressure/flow controlling mechanism; and
c) a tube for conveying gas therethrough having a first end and a second end; the first end adapted for placement in the cardiovascular system of the animal and having a plurality of apertures for passage of the gas therethrough; and the second end adapted for connection to the outlet end of the filter;
wherein the connections between the pressure/flow controlling mechanism, the filter, and the gas conveying tube provide a fluid communication for conveying the gas therethrough.

15. The assembly according to claim 14, further comprising a component selected from the group consisting of
a tube for removing fluid from the cardiovascular system having a first end and a second end; the first end adapted for placement in the cardiovascular system of the animal, and the second end adapted for connection to a mechanism operable to draw the fluid out of the cardiovascular system and through the fluid removal tube; and
a tube having a first end and a second end; the first end connectable to the second end of the gas conveying tube, and the second end adapted for connection to the outlet end of the filter.

16. The assembly according to claim 14, further comprising:
a check-valve adapted for insertion into the gas conveying tube, and operable to prevent blood from flowing from the heart into the tube.

17. The assembly according to claim 14, further comprising, at least one of:
a mechanism operable to draw fluid thereinto, having an inlet end adapted for connection to the second end of the fluid removal tube;
a mechanism for imaging gas bubbles in the body of the animal; and
a source of gas having an outlet end adapted for connection to the inlet end of the gas pressure/flow controlling mechanism.

18. The assembly according to claim 14, wherein the gas conveying tube is integrated with a balloon endoaortic catheter.

19. A method of preventing an air embolism in the brain of an animal in a cardiovascular surgical procedure, comprising:
a) providing a system comprising:
i) a source of gas;
ii) a mechanism for controlling pressure and flow of the gas therethrough, having an inlet end and an outlet end, the inlet end being connected to the gas source;
iii) a tube for conveying the gas therethrough into the cardiovascular system, having a first end and a second end, and a member for preventing blood from flowing from the heart into the carbon dioxide conveying tube; the first end adapted for placement in the cardiovascular system of the animal and having a plurality of apertures for passage of the gas therethrough; and the second end adapted for connection to the pressure and flow controlling mechanism; and
iv) a tube for removing fluid from the cardiovascular system, having a first end, a second end, and a central channel therethrough; the second end connected to a mechanism operable to draw fluid through the central channel;
wherein the gas source, the pressure/flow controlling mechanism and the gas conveying tube are in fluid communication for conveying the gas therethrough, with the pressure/flow controlling mechanism disposed between the gas source and the gas conveying tube;

b) placing the first ends of the gas conveying tube and the fluid removing tube into the cardiovascular system;

c) administering the gas into the cardiovascular system at a pressure and flow effective to purge air from the cardiovascular system; and removing fluid from the cardiovascular system via the fluid removing tube;

d) reducing the flow of the gas into the cardiovascular system; and e) removing the gas conveying tube and the fluid removing tube from the cardiovascular system.

20. The method according to claim 19, wherein the cardiovascular system is the heart, and the gas conveying tube and the fluid removing tube are placed into the left ventricle of the heart.

21. The method according to claim 20, wherein step b) further comprises:

inserting a tube into an opening in the aorta, and aspirating the purged air and gas through the tube.

22. The method according to claim 21, wherein step b) is performed prior to the surgical procedure, and the method further comprises prior to step d):

allowing the left ventricle to fill with blood while administering the gas to purge the air therefrom through the opening in the aorta; and closing the surgical wound.

23. The method according to claim 21, wherein step b) is performed prior to the surgical procedure, and the method further comprises prior to step d):

closing the surgical wound; and administering the gas to purge the air from the left ventricle through the opening in the aorta; and removing fluid from the left ventricle via the fluid removing tube.

24. The method according to claim 19, wherein the cardiovascular system is a great vessel selected from the group consisting of the aorta, a heart artery, a carotid artery, an axillary artery, and a pulmonary vein.

25. The method according to claim 19, wherein step c) comprises administering the gas at a pressure of about 30–100 mmHg.

26. The method according to claim 19, wherein step d) comprises administering the gas at a pressure of about 5–20 mmHg.

27. The method according to claim 19, wherein step c) further comprises:

conveying the fluid removed from the cardiovascular system to a device for treating the blood to remove dissolved gas, add oxygen, or both; and transmitting the treated blood into the animal.

28. The method according to claim 19, further comprising:

monitoring the amount of gas bubbles in the blood of the animal.

29. The method according to claim 28, wherein step b) is performed after the completion of the surgical procedure, and the method further comprises prior to step c):

the step of closing the surgical wound.

30. A system for preventing an air embolism in the brain of an animal in a cardiovascular surgical procedure, comprising:

a source of carbon dioxide;

a mechanism for controlling pressure and flow of the carbon dioxide therethrough, having an inlet end and an outlet end, the inlet end being connected to the carbon dioxide source; and a multiple lumen tube having first and second channels defining a fluid removal tube and a carbon dioxide conveying tube, each tube having a first and second end, the first ends adapted for placement in the heart of the animal;

the carbon dioxide conveying tube having a plurality of apertures in the first end for passage of carbon dioxide therethrough into the heart, and the second end being connectable to the outlet of the pressure and flow controlling mechanism the fluid removal tube having an opening in the first end for passage of fluid therethrough from the heart, and the second end being connectable to a mechanism operable to draw the fluid out of the heart through the fluid removal tube;

wherein the carbon dioxide conveying tube has a smaller inside diameter than the fluid removal tube;

the pressure/flow controlling mechanism is disposed between the gas source and the gas conveying tube; and the gas source, the pressure/flow controlling mechanism and the gas conveying tube are in fluid flowing communication for conveying the gas therethrough;

and the pressure/flow controlling mechanism is operable to provide a flow of the gas through the system such that when the first end of the gas conveying tube is placed into the heart, the pressure and flow of the gas from the pressure/flow controlling mechanism through the gas conveying tube into the heart is effective to inhibit air from entering the heart, great vessel, or both, or to remove air from the heart, the great vessel, or both.

31. The system according to claim 30, wherein the first end of the fluid removal tube extends beyond the first end of the carbon dioxide conveying tube.

32. The system according to claim 31, wherein the first end of the carbon dioxide conveying tube is about 1–2 inches shorter than the first end of the fluid removal tube.

33. The system according to claim 30, wherein the carbon dioxide conveying tube is terminated with a slanted end.

34. The system according to claim 30, wherein the multiple lumen tube is part of a balloon endoaortic catheter.

* * * * *